United States Patent
Arduini

(10) Patent No.: US 6,822,002 B1
(45) Date of Patent: Nov. 23, 2004

(54) USE OF L-CARNITINE AND ITS ALKANOYL DERIVATIVES AS OSMOTIC AGENTS IN SOLUTIONS FOR MEDICAL USE

(75) Inventor: Arduino Arduini, Rome (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 10/110,304

(22) PCT Filed: Oct. 11, 1999

(86) PCT No.: PCT/IT99/00317

§ 371 (c)(1), (2), (4) Date: May 21, 2002

(87) PCT Pub. No.: WO01/26649

PCT Pub. Date: Apr. 19, 2001

(51) Int. Cl.[7] .................. A61K 31/14; A61K 31/32; C12P 13/00

(52) U.S. Cl. ............ 514/642; 424/311; 435/128; 514/561; 514/563; 514/689

(58) Field of Search .............. 514/642, 561, 514/689, 563; 424/311; 435/128

(56) References Cited

U.S. PATENT DOCUMENTS

| | | | |
|---|---|---|---|
| 4,237,167 A | 12/1980 | Cavazza | 424/311 |
| 4,272,549 A | 6/1981 | Cavazza | 424/316 |
| 4,708,936 A * | 11/1987 | Kulla et al. | 435/128 |
| 5,973,004 A * | 10/1999 | Howard | 514/561 |
| 6,440,449 B1 * | 8/2002 | Hirschberg | 424/439 |
| 6,482,585 B2 * | 11/2002 | Dottori | 435/2 |
| 6,537,976 B1 * | 3/2003 | Gupta | 514/52 |

FOREIGN PATENT DOCUMENTS

| | | |
|---|---|---|
| EP | 0 627 161 A | 12/1994 |
| GB | 2 059 262 A | 4/1981 |
| WO | 99/07419 A | 2/1999 |

OTHER PUBLICATIONS

B.A. Warady E.A.: "Carnitine Status of Pediatric Patients on Continuous Ambulatory Peritoneal Dialysis" American Journal of Nephrology; vol. 10, No. 2, 1990 pp. 109–114, XP000921067.

* cited by examiner

Primary Examiner—Vickie Kim
(74) Attorney, Agent, or Firm—Nixon & Vanderhye P.C.

(57) ABSTRACT

The use of L-carnitine and its alkanoyl devivatives, optionally in the form of a pharmaceutically acceptable salt, as osmotic agents in the preparation of solutions for medical use, particularly for peritoneal dialysis, is described.

13 Claims, No Drawings

USE OF L-CARNITINE AND ITS ALKANOYL DERIVATIVES AS OSMOTIC AGENTS IN SOLUTIONS FOR MEDICAL USE

This application is the US national phase of international application PCT/IT99/00317 filed 11 Oct. 1999, which designated the US.

The invention described herein relates to the use of L-carnitine and its alkanoyl derivatives, optionally in the form of a pharmaceutically acceptable salt as osmotic agents in solutions for medical use, particularly in peritoneal dialysis.

BACKGROUND OF THE INVENTION

Patients suffering from end-stage renal disease (or ESRD) must either undergo dialysis therapy or be submitted to a kidney transplant. Both therapeutic interventions are extremely demanding, both from the point of view of the quality of life of the patient and in terms of social costs. For a review of dialytic therapy see, for example, Pastan S. and Bailey J. in the New England Journal of Medicine, 14 May 1998, pp. 1428–1436, incorporated herein for reference in its entirety.

Dialytic therapy comprises two types of treatment, namely peritoneal dialysis and haemodialysis. There are major differences between the two types of dialysis, such as, in the case of haemodialysis, the cost of the therapy, the need for dedicated departments with expensive equipment and qualified staff, and the quality of life of the patient. Peritoneal dialysis, on the other hand, enjoys greater favour on account of its simplicity of execution, which can be handled by the patient himself in the form of self-medication. In Italy, for example, 15% of dialysis patients use peritoneal dialysis, which is practically the same as in the USA (16%), while the percentages of patients on peritoneal dialysis are higher in Canada (38%) and the United Kingdom (52%), and get up to as much as 90% in Mexico. The reason for these different rates is also to be attributed to the lower cost of peritoneal dialysis as compared to the cost of haemodialysis which not all national health systems are prepared to bear. We should, however, not overlook the fact that peritoneal dialysis allows the patient to maintain a less constrained life-style, since the dialysis session can be planned with a certain measure of autonomy in the course of the person's normal activities. In addition, automatic devices also allow dialysis during the hours of the night.

Despite this, the choice between the two types of dialysis is not a free one; for instance, peritoneal dialysis is indicated for patients with cardiac insufficiency or unstable angina who cannot support the alterations of blood flow and/or arterial blood pressure that accompany the haemodialysis session (see reference cited above).

One can postulate a therapeutic progression for the ESRD patient which starts with peritoneal dialysis, proceeds via haemodialysis and finally reaches a stage where a kidney transplant is needed.

Peritoneal dialysis is not without disadvantages and unwanted adverse effects. These drawbacks can be placed in two distinct, even if related, categories, namely adverse clinical effects and technological problems. The purpose of the invention described herein is to remedy these disadvantages and adverse effects.

In the typical execution of a peritoneal dialysis session, a plastic catheter is implanted in the peritoneal cavity and anchored to the subcutaneous tissues. A dialysis solution contains physiological amounts of sodium, calcium, magnesium, compatible physiological buffer and a non-toxic osmotic agent, of such a nature as to make the solution hyperosmolar as compared to the plasma. The solution is infused via the catheter into the peritoneal cavity where it then remains for several hours. During this time, the peritoneal membrane exchanges solutes by diffusion in such a way as to obtain replacement with fresh fluid. Given that renal function decreases in the first few years of dialysis, the dose of dialysis fluid to be exchanged increases in the course of time.

Peritonitis is the serious complication that occurs most frequently. Other types of complications are losses of amino acids and albumin, incompatibility of the dialysis solution, volume effects in the peritoneal cavity, metabolic consequences, symptoms affecting the digestive tract, reduced appetite and others (for a review see C. M. Mion, R. and Gokal and N. P. Mallick, Lancet, 1999; 353; 823–28).

One of the most pressing problems in the peritoneal dialysis sector is the choice of a suitable osmotic agent.

The requisites of an ideal solution for peritoneal dialysis include:
- supplying the nutritional requirement and avoiding adverse metabolic effects;
- ensuring minimal absorption of the osmotic agent, which, in any case, must be non-toxic;
- being capable of correcting acidosis and having a physiological pH;
- in addition to considerations with technological implications, such as apyrogenicity, absence of metals and residues of synthetic materials, the solution must also inhibit bacterial and fungal growth, must not damage the immune defences and must be inert in relation to the peritoneal membrane. A typical solution for peritoneal dialysis contains glucose in various concentrations as an osmotic agent, and various amounts of lactate (which has replaced acetate owing to problems of intolerance on the part of the patient), sodium, potassium and calcium. Buffer systems have also been studied in an attempt to solve the problem of sterilization and stabilization of the solution.

As regards the sterilization aspect, this is a critical technological problem; in fact, heat sterilization, commonly used in the sector of solutions for medical use, causes degradation of glucose, with consequent production of toxic secondary derivatives, such as aldehydes and 5-hydroxymethylfurfural. Traditionally heat sterilization of the solution containing glucose (also indicated as dextrose) is done at a pH between 5.0 and 5.5, precisely in order to avoid caramelization of the glucose. The acid pH leads to further problems for the patient using the solution, such as, for example, abdominal pain and sclerosis of the peritoneal membrane, which entails a reduction of the elimination of solutes (Schmidt et al., Arch. Int. Med., 141; 1265–1266, 1981).

The purpose of the invention described herein is also to provide a solution to the complex problems related to the use of glucose as an osmotic agent in solutions for peritoneal dialysis.

Glucose is extensively used owing to its great availability on the market and its low cost. It is a relatively safe substance, but its use at high concentrations and its prompt absorption lead to short ultrafiltration times, and metabolic complications, such as hyperinsulinaemia, hyperlipidaemia, and weight gain. In addition, hyperosmolarity and low pH can damage the mesothelium and macrophages. Moreover, the potential glycosylation of stromal proteins leads to further damage to the peritoneum. Also reported is the inhibition of phagocytosis, bactericidal activity and the synthesis of $LTB_4$ in peripheral blood neutrophils. In continuous ambulatorial peritoneal dialysis (CAPD), where the application time can be as much as 6 hours or more, the glucose concentrations are very high to be able to maintain the ultrafiltration capacity. For a review of the biocompatibility of solutions for peritoneal dialysis see C. J. Holmes in Peritoneal Dialysis International, Vol. 13, pp. 88–94, 1993.

To overcome the problems created by the use of glucose as an osmotic agent in peritoneal dialysis, the state of the art directs experts in the field towards two distinct types of solution:

1) the use of low-molecular-weight osmotic agents, capable of sustaining ultrafiltration with minimal metabolic effects, without, however, altering the ultrafiltration profile;
2) the use of high-molecular-weight osmotic agents in an attempt to act on both factors.

Of the various low-molecular-weight agents proposed, to date only glycerol and mixtures of amino acids would appear to be of a certain clinical interest. In Italy, for example, a 1.1% multi-amino-acid solution is being marketed by Baxter under the trade mark Nutrineal® PD2 and PD4.

These proposed alternatives to glucose are not problem-free; other saccharides have metabolic effects: for example, fructose gives rise to hypertriglyceridaemia and hyperosmolarity, sorbitol hyperosmolarity and accumulation, xylitol lactic acidosis and hyperosmolarity; glycerol is well tolerated, but its ultrafiltration capacity is short-lasting and it also causes hyperosmolarity, while an adverse effect on phagocytes has also been reported (de Fijter CWH et al., Advances in Continuous Ambulatorial Peritoneal Dialysis, Toronto, Peritoneal Dialysis Publication, 1991, 154–7). Amino acids, though useful in undernourished patients, give rise to acidosis and to an increase in the nitrogen load, which is contraindicated in an uraemic patient. On the other hand, high-molecular-weight osmotic agents present a whole series of disadvantages of their own, such as possible immunogenicity in the case of peptides, absorption, intraperitoneal bleeding (demonstrated in rats) and ultrafiltration in the case of dextrans (MW 60–200 kDa), cardiovascular instability, peritoneal damage and haemorrhage in the case of polyanions and cations (MW 40–90 kDa), prolonged half-life, immunogenicity, allergenicity and high viscosity of the solution in the case of gelatines (MW 20–390 kDa) and maltose retention in the case of glucose polymers.

Unfortunately, the adverse effects of solutions for peritoneal dialysis do not stem only from the osmotic agent chosen, but also from other components of the solutions. Lactate, for example, when combined with the low pH of the solution, which is necessary in order to be able to perform sterilization, suppresses various functional activities of the peripheral and peritoneal leukocytes and inhibits the production of IL-6 and TNFα by mononuclear cells.

In his review of osmotic agents, Gokal concluded in 1990 that at that time there was no osmotic agent capable of replacing glucose (Coles G A, Davies M, Williams J D (eds): CAPD: Host Defence, Nutrition and Ultrafiltration. Contrib. Nephrol., Basel, Karger, 1990, vol. 85, pp. 126–133).

An enormous effort is being made to find an alternative osmotic agent to glucose, meeting or at least coming close to meeting the requisites of the "ideal" solution. Among the numerous patent references, we should cite patent JP 11071286, filed in the name of the Terumo Corp., which describes a solution where the osmotic agent consists in a mixture of glucose and maltose in molar ratios of 1:0.05–5 and with an osmotic pressure of 280–600 mOsm/kg at pH 6.0–7.5, with enhanced water removal characteristics and reduced glucose absorption. For obese, diabetic patients, the same company supplies a complex osmotic agent, made up of N-acetylamine acid (L-amino acid), N-acetyl-D-glucosamine, glucuronic and/or ascorbic acid (patent JP 11071273). Mixtures of saccharides with hexavalent alicyclic alcohols, hexonic acid and sacchric acid are described in patent JP 11049671, filed in the name of Baxter Int. Inc. Patent application WO 9901144, filed by Allied Therapeutics Ltd., describes synthetic hydrogenated di- and trisaccharides. Patent MX 9601855, filed by Trevino, uses dextran 60. Baxter again, in patent JP 10094598, proposed non-reducing oligosaccharides or polysaccharides containing from 3 to 12 residues. In patent application WO 9801141, filed by Bieffe Medital SpA, the use of glycosaminoglycans, devoid of anticoagulant or haemorrhagic activity, is described. U.S. Pat. Nos. 5,629,025, 5,589,197 and 5,631,025, filed in the name of Baxter International Inc., describe solutions for peritoneal dialysis with a low sodium content, for which substances containing at least one amino acid or polypeptide, or a polyglucose, are envisaged as osmotic agents. The University of Missouri supplies chemically crosslinked gelatine as an osmotic agent to partially or wholly replace glucose (U.S. Pat. No. 4,604,379). Starch hydrolysates are described in U.S. Pat. No. 5,837,060, filed in the name of Roquette Freres. Patent JP 7323084, filed by Morishita Roussel KK and Ajinomoto Co. Inc., describes the use of trehalose to prepare neutral solutions to replace glucose. See also U.S. Pat. No. 4,761,237.

Examining in greater detail the low-molecular-weight osmotic agents to which the present invention refers, the state of the art provides teachings directed to the use of amino acids or short peptides, which are advantageous from the point of view of the nutritional support of undernourished patients. Baxter International Inc., under its U.S. Pat. No. 5,776,503, supplies a mixture of amino acids, which is highly complex but, despite its very high cost, has yet to be surpassed by the many alternatives proposed. U.S. Pat. No. 5,780,438, filed in the name of Giltech Limited, describes a stable solution, where the osmotic agent consists of a mixture of peptides obtained from the proteolysis of casein or whey proteins. U.S. Pat. No. 5,869,444, filed in the name of Research Corporation Technologies, extensively discusses the alternatives to glucose and directs the experts in the field towards low-molecular-weight osmotic agents of an amino-acid nature. However, though admitting the nutritional benefit, mentioned earlier, the inventors stress the disadvantage of the high cost, and the increased nitrogen load in the blood. Thus, in the cited patent, they propose the use of oligopeptides (300–2000 Da) derived from the enzymatic hydrolysis of high-quality proteins, such as whey, which are advantageous both from the functional point of view of the dialysis and from the nutritional point of view. In this patent, however, the need is perceived for a very thorough and carefully controlled hydrolysis and separation process in order to avoid the risk of high-molecular-weight components, potential antigens or allergens. Among the protein sources, those mentioned include collagen, the use of which today is, however, questionable owing to problems of prion contamination (BSE, scrapie), milk proteins, but not casein, and others. In the course of the description, the inventors admit a series of difficulties in assuring the quality of the hydrolysis process.

In relation to other aspects of peritoneal dialysis, DE 19748290, WO 991762, JP 10330270, WO 9852599, WO 9850060, CA 2219822, WO 9917762 and U.S. Pat. No. 5,827,820 are cited.

All documents cited are incorporated herein for reference in their entirety.

ABSTRACT OF THE INVENTION

It has surprisingly been found that L-carnitine, or, alternatively, one of its lower alkanoyl derivatives, or L-carnitine in combination with its lower alkanoyl derivatives, is useful as an osmotic agent in the preparation of solutions for peritoneal dialysis, and in general as an osmotic agent for solutions for medical use.

One subject of the invention described herein is the use of L-carnitine and its lower alkanoyl derivatives, where what is meant by lower alkanoyl derivative is a straight or branched aliphatic acylic residue with from 2 to 8 carbon atoms, optionally in the form of a pharmaceutically acceptable salt, as an osmotic agent in solutions for medical use, particularly for the preparation of solutions for peritoneal dialysis. Another subject of the present invention consists in solutions for medical use characterised in that the osmotic agent is L-carnitine or one of its alkanoyl derivatives, as defined above, optionally in combination with one another or with one or more known osmotic agents.

L-carnitine and its lower alkanoyl derivatives are known to have various therapeutic uses. In particular, U.S. Pat. No. 4,327,167, filed in the name of the applicant, describes the use of alkanoyl carnitines, as defined above, in a therapeutic method for the treatment of chronic uraemic patients undergoing regular dialysis. Also described are polysaline solutions for haemodialysis containing an alkanoyl carnitine. Patent EP 0793962, filed in the name of the applicant, describes the use of propionyl L-carnitine for the preparation of a medicine useful for the selective treatment of chronic obliterating atherosclerosis (claudicatio intermittens). Patent IT 1155772, filed in the name of the applicant, describes the use of alkanoyl L-carnitine in the therapy of myocardial anoxia, ischaemia, arrhythmia syndromes and heart failure. U.S. Pat. No. 4,255,449, filed in the name of the applicant, describes the use of L-carnitine in the treatment of dyslipidaemias. Patent application WO 9906039, filed in the name of the applicant, describes the use L-carnitine and its alkanoyl derivatives in combination with polycosanols for the treatment of dyslipidaemias. There are numerous descriptions of combinations of L-carnitine and alkanoyl derivatives with other active ingredients, e.g. gamma-linoleic acid (see WO 9841113) for the treatment and prevention of the side effects of diabetes mellitus, particularly peripheral neuropathy.

U.S. Pat. No. 4,272,549 teaches the use of particular administration regimens of L-carnitine combined orally and intravenously to combat post-dialysis syndrome in uraemic patients undergoing regular haemodialysis treatment.

U.S. Pat. No. 4,237,167 teaches the use of particular administration regimens of acyl L-carnitine combined orally and intravenously to combat post-dialysis syndrome in uraemic patients undergoing regular haemodialysis treatment.

Patent application WO 9907419, filed in the name of Gupta, describes compositions for dialysis containing an effective amount of at least one vitamin selected from the group consisting of folic acid, vitamin $B_6$, thiamine, vitamin $B_{12}$, and optionally vitamin C and/or carnitine. The purpose of these preparations is to compensate for the loss of vitamins to which patients on either haemodialysis or peritoneal dialysis are subject. The effective amounts are indicated in the description. In the case of free L-carnitine, an amount less than 50 $\mu$mol/l is specified for the dialysed patient during each dialysis session for the prevention of vitamin and carnitine deficiencies. The preferred concentrations range from 50 to 300 $\mu$mol/l. Thus, the amount of L-carnitine present in the solutions described by Gupta is less than the amount necessary for L-carnitine to act as an osmotic agent.

The advantages of using L-carnitine or one of its alkanoyl derivatives, as defined above, are multiple. The replacement of glucose by L-carnitine or one of its alkanoyl derivatives eliminates the adverse effects described above. Furthermore, the carnitines (meaning L-carnitine or its alkanoyl derivatives as defined in the invention described herein) are compatible with the bicarbonate buffer, and therefore obviate the disadvantage of having to use solutions at below physiological pH, such as the pH 5.0 or 5.5 typical of glucose solutions.

The use of carnitines, particularly L-carnitine, acetyl L-carnitine and propionyl L-carnitine, is additionally advantageous compared to other known osmotic agents because the carnitines are non-toxic, well tolerated substances with no adverse effects at the doses described below. Unlike the amino acids, the carnitines play no part in protein metabolism and thus do not aggravate the nitrogen load of the uraemic patient. As regards the difference from high-molecular-weight osmotic agents, the advantage is immediate: the carnitines are natural substances present in living organisms, particularly mammals, including man. For this reason, the risk of introducing xenobiotic substances into the body is eliminated.

Moreover, the use of carnitines as osmotic agents provides the dialysed patient with the amount of L-carnitine necessary to compensate for the carnitine losses which occur during the dialysis session. For data on carnitine levels in patients undergoing CAPD, see Kidney Int. 1996 January; 49(1): 158–62 and Perit. Dial. Int. 1993; 13 Suppl 2.

A further advantage of the application of the invention described herein is that carnitine, when used as an osmotic agent, not only compensates for the carnitine losses, but is also capable of exerting its own therapeutic effects in a series of diseases related to renal insufficiency, such as, for example, the diseases described in the above-mentioned patents.

The invention will now be described in detail also with the aid of examples. Further subjects of the invention described herein, with their respective advantages, will be apparent to experts in the field to which the present invention pertains.

DETAILED DESCRIPTION OF THE INVENTION

What is meant by lower alkanoyl is an acyl group with from 2 to 8 carbon atoms, preferably from 2 to 6, such as acetyl, propionyl, butyryl, isobutyryl, valeryl, isovaleryl, 2-methyl-butyryl, 2,2-dimethylpropionyl, hexanoyl, heptanoyl, octanoyl and all their possible isomers.

The invention described herein envisages the use of carnitines as inner salt. If deemed suitable, one of their pharmaceutically acceptable salts can be used. What is meant by pharmaceutically acceptable salt of L-carnitine or of an alkanoyl L-carnitine derivative is any salt of the latter with an acid which does not give rise to unwanted toxic or side effects. These acids are well known to pharmacologists and to experts in pharmaceutical technology.

Examples of pharmaceutically acceptable salts of L-carnitine or alkanoyl L-carnitines, though not exclusively these, are chloride, bromide, orotate, acid aspartate, acid citrate, acid phosphate, fumarate and acid fumarate, maleate and acid maleate, acid oxalate, acid sulphate, glucose phosphate, tartrate and acid tartrate. The preferred salts are those with fumarate, aspartate, citrate and maleate.

Also the subject of the invention described herein are solutions for peritoneal dialysis, both in the form of ready-to-use solutions and in the form of concentrates to be diluted at the time of use, containing an osmotic agent according to the present invention.

The dosages, posology and treatment regimen in general will be determined by the primary care physician according to his knowledge of the case, the patient's condition and the extent of the disease to be treated.

In a first preferred realization, in the invention described herein L-carnitine, inner salt, is used.

In a second preferred realization, carnitine is present in the form of a salt with fumaric acid. Though not wishing to be bound by any theory, the applicant believes that the fumarate salt may be particularly advantageous for supplying the energy requirement of the dialyzed patient. Fumarate, in fact, is an energy substrate which is useful in the treatment of organ ischaemia. The applicant has demonstrated the efficacy of L-carnitine fumarate in the treatment of organ ischaemia, particularly ischaemic heart disease, as described in patent application 99RM0003328, incorporated herein for reference in its entirety.

In a third realization of the invention described herein, a combination of L-carnitine and acetyl L-carnitine is used. This combination is additionally advantageous to provide the patient with an acetyl L-carnitine supplement.

In the description of the possible realizations of the invention, what is meant by carnitine is L-carnitine, as inner salt, or a salt with a pharmaceutically acceptable acid, as described above, alone or in combination with one of its alkanoyl derivatives as inner salt, or as a salt with a pharmaceutically acceptable acid, or one of its alkanoyl derivatives, as inner salt or a salt with a pharmaceutically acceptable acid.

In a first aspect of the present invention, carnitine is used as an osmotic agent as a total substitute for glucose.

The carnitine concentrations are those sufficient for it to act as an osmotic agent and concentrations up to a physiologically tolerable maximum are envisaged. It is understood that the carnitine concentration will be such as to ensure a satisfactory effect for the uses envisaged for the present invention. In particular, it is considered satisfactory the obtained which can be considered a therapeutic effect in the context of peritoneal dialysis.

Where not otherwise specified, the concentrations are understood to be weight/volume (w/v).

Examples of concentrations are approximately 0.5 to approximately 10%, preferably approximately 0.7 to approximately 7%, and more preferably from approximately 1 to 5%. In a typical realization of the present invention, the carnitine concentrations are those normally used for glucose in commercial preparations, namely from 1.5 to 4.25%.

It is understood that experts in the field will be capable of determining effective concentrations according to the type of solution used. Examples are concentrations starting from approximately 0.5%.

If so required, alternatively, carnitine can be used as a partial substitute for glucose. The respective carnitine and glucose concentrations can be freely varied, provided that a satisfactory effect is obtained in terms of the uses envisaged for the present invention. Examples of combinations with glucose are 4.0% glucose-0.25% carnitine; 1.0% glucose-0.5% carnitine; 0.5% glucose-1.0% carnitine; 0.25% glucose-4.0% carnitine. The 0.5% glucose-1.0% carnitine combination is preferred.

Other possible realizations of the invention consist in a combination of carnitine as an osmotic agent with other known osmotic agents; for example, preferred combinations are those with amino acids, such as the formulations already present on the market, or with the dipeptides and/or polypeptides of the above-mentioned patents. One particularly advantageous realization is the use of carnitine in the twin bags described in patent DE 19748290, which uses bicarbonate buffer. It is also useful to increase the dose of carnitine, particularly L-carnitine, in the solutions described in WO 9907419 up to a concentration which is effective as an osmotic agent.

In another possible realization, the osmotic agent according to the present invention is used in combination with the osmotic agents described in U.S. Pat. No. 5,827,820, filed in the name of Baxter International Inc.

The use of the osmotic agent according to the present invention is also envisaged in combination with high-molecular-weight osmotic agents, such as, for instance, those described in the above-cited references, and particularly with icodextrin.

In a particular realization of the present invention, a surfactant normally used in this field is added to the peritoneal dialysis solution. Specific mention is made of palmitoyl L-carnitine.

One specific subject of the present invention consists in solutions for medical use characterized in that the osmotic agent is L-carnitine and/or its alkanoyl derivatives, in which the alkanoyl is a straight or branched aliphatic residue with from 2 to 8 carbon atoms, optionally in the form of a pharmaceutically acceptable salt. A particular subject of the present invention consists in solutions for peritoneal dialysis.

As regards those aspects pertaining to industrial applicability, the solutions which are the subjects of the present invention will be contained in suitable containers for peritoneal dialysis, generally bags made of suitable material compatible with medical use. Containers for peritoneal dialysis are known to experts in the field and do not require any particular description, the reader being referred to the specific literature and to the general knowledge of the technical field to which the invention pertains. Examples are bags with a single chamber or multiple chambers, e.g. a double chamber, or separate bags containing different solutions to be mixed at the time of use by means of automatic equipment. Containers for peritoneal dialysis containing a solution according to the present invention are covered by the protection afforded by the present patent application.

The invention described herein is now described with the aid of experimental tests permitting the implementation of the the realization preferred. It is fully understood that equivalent realizations coming within the framework of the present invention can be implemented by the person having ordinary skill in the field, availing himself only of his own general knowledge, even by the trial and error method, without any need for further description on the part of the present invention.

In-vitro Transport Studies

Fluid transport in vitro was performed using tubes consisting of semipermeable cellulose membranes containing the various different dialysis solutions.

Buffer solutions were added with scalar concentrations of carnitine (0.5, 1.0 and 1.5%) in bicarbonate buffer (30 mM) and NaCl (100 mM) at pH 7.2. A 1.5% glucose solution was used as a reference.

The composition of the buffer solution is as follows: sodium 134 mmol/l, calcium 1.75 mmol/l, magnesium 0.5 mmol/l. The solutions containing glucose were buffered at pH 5.5 with 35 mmol/l of L-lactate. The solutions containing carnitine were buffered as for glucose at pH 7.0–7.6 with 34 mmol/l of bicarbonate. Ten ml of the various dialysis solutions were placed in the tubes and the tubes were suspended in a 1liter graduated cylinder filled with a 0.9% NaCl solution. The saline bath was recycled at a rate of 500 ml/min with direct flow along the main axis of the dialysis tube using an infusion pump. The amount of fluid recovered inside the tube was determined gravimetrically after removing the fluid adhering to the walls of the membrane with a sheet of absorbent paper. The tube was then put back inside the cylinder and submitted to successive weight measurements at 15, 30, 45, 60, 90, 120, 180, 240, 300 and 360 minutes.

Table 1 gives the increase in weight of the fluid recovered the dialysis solution in the course of time.

TABLE 1

Fluid transport induced by 10 ml of fluid containing different concentrations of carnitine or glucose.

| Times (min) | Carnitine 0.5% (g fluid) | Carnitine 1.0% (g fluid) | Carnitine 1.5% (g fluid) | Glucose 1.5% (g fluid) |
|---|---|---|---|---|
| 15  | 0.02 ± 0.01 | 0.07 ± 0.02 | 0.10 ± 0.01 | 0.09 ± 0.02 |
| 30  | 0.06 ± 0.01 | 0.13 ± 0.02 | 0.26 ± 0.03 | 0.19 ± 0.03 |
| 45  | 0.10 ± 0.03 | 0.20 ± 0.03 | 0.30 ± 0.02 | 0.27 ± 0.02 |
| 60  | 0.12 ± 0.02 | 0.22 ± 0.03 | 0.35 ± 0.04 | 0.31 ± 0.04 |
| 90  | 0.17 ± 0.03 | 0.33 ± 0.03 | 0.48 ± 0.04 | 0.41 ± 0.04 |
| 120 | 0.19 ± 0.02 | 0.36 ± 0.03 | 0.54 ± 0.04 | 0.47 ± 0.04 |
| 180 | 0.21 ± 0.03 | 0.42 ± 0.04 | 0.66 ± 0.04 | 0.54 ± 0.04 |
| 240 | 0.27 ± 0.02 | 0.49 ± 0.03 | 0.77 ± 0.05 | 0.59 ± 0.04 |
| 300 | 0.29 ± 0.02 | 0.51 ± 0.03 | 0.77 ± 0.04 | 0.63 ± 0.05 |
| 360 | 0.27 ± 0.03 | 0.48 ± 0.04 | 0.74 ± 0.05 | 0.62 ± 0.04 |

The values are means (n=3)±S.D. of 3 different experiments.

The weight of the dialysis tube increases progressively over time as a function of the different carnitine concentrations. The plateau is reached for all concentrations assayed at 240 minutes. The trend of the samples containing 1.5% glucose is comparable to that of the samples containing 1.5% carnitine.

In-vivo Experiments

The peritoneal dialysis experiment was conducted in male Sprague-Dawley rats weighing 500–600 g (Charles River) maintained on a standard diet with water ad libitum. The animals were anaesthetized with an intraperitoneal injection of inactin (100 mg/kg) and were placed on an operating table at controlled temperature. The animals were submitted to a tracheostomy to cannulate the left jugular vein with a PE50 medical silicone tube. Thirty minutes after administration of the anaesthetic the animals were infused with a saline solution at a rate of 2.3 ml/h throughout the period of the experiment. The dialysis solution (15 ml), after preheating to 37° C., was inoculated into the peritoneal cavity with a 15 teflon needle-cannula 1 h after administration of the anaesthetic. The amount of fluid injected was determined by weighing the syringe before and after injection of the fluid, using an electronic scale. At the end of each analysis period (2, 4 and 6 h), incisions were made in the rats' abdomens with an acusector and all the fluid present in the peritoneum was aspirated with a 1 ml syringe. After removing the surface fluid, the intestines were carefully shifted from the abdominal cavity to collect the residual fluid remaining on the dorsal wall. The fluid recovered was placed in a beaker and weighed. The change in weight compared to time 0 represented the amount of fluid recovered from the peritoneal solution injected.

A series of in-vivo experiments was conducted according to the experimental model described above in order to evaluate the transport ability of various dialysis fluids containing carnitine.

The data relating to initial and final weight of the fluid recovered from the peritoneum of the animals at the different analysis times were used to calculate the percentage increase in volume in each animal.

Table 2 gives the data for an experiment in which glucose was used at different concentrations (1.5, 2.5 and 4.25%) as the dialysis fluid. These hyperosmolar solutions constitute our control data since they are those commonly used in clinical practice.

TABLE 2

Percentage changes in fluid volume recovered from rats submitted to peritoneal dialysis with 15 ml of solution containing different concentrations of glucose.

| Solutions | % increase in volume (2 h) | % increase in volume (4 h) | % increase in volume (6 h) |
|---|---|---|---|
| Glucose 1.5%  | 21.1 ± 1.5 | 21.5 ± 1.9 | 21.7 ± 1.6 |
| Glucose 2.5%  | 35.2 ± 1.4 | 35.9 ± 1.3 | 36.8 ± 1.5 |
| Glucose 4.25% | 59.8 ± 1.6 | 60.5 ± 1.7 | 59.1 ± 1.6 |

Results are expressed as mean (n=3)±S.D.

Glucose at all concentrations used causes an increase in intraperitoneal fluid volume which is completed in the first 2 h. In fact, at 4 and 6 h the fluid volume in the peritoneum remains constant.

The same experiment was conducted using scalar concentrations of carnitine. The results are given in Table 3.

TABLE 3

Percentage changes in fluid volume recovered from rats submitted to peritoneal dialysis with 15 ml of solution containing different concentrations of carnitine.

| Solutions | % increase in volume (2 h) | % increase in volume (4 h) | % increase in volume (6 h) |
|---|---|---|---|
| Carnitine 1.5%  | 25.8 ± 1.3 | 22.5 ± 1.6 | 25.3 ± 1.4 |
| Carnitine 2.5%  | 38.1 ± 1.4 | 37.3 ± 1.4 | 38.5 ± 1.6 |
| Carnitine 4.25% | 61.5 ± 1.5 | 64.1 ± 1.8 | 62.3 ± 1.9 |

Results are expressed as mean (n=3)±S.D.

Carnitine, too, proves to be a good osmotic agent, at least as good as glucose. The percentage increase in intraperitoneal fluid volume is slightly greater than that produced by glucose. The fluid recovery by the solution containing carnitine is also rapid in this case and reaches peak activity within 2 h, producing no further increases in volume at the later observation times (4, 6 h).

After confirming the activity of carnitine as an osmotic agent for peritoneal dialysis in vivo, we conducted a series of experiments using carnitine in mixtures with glucose or amino acids (aa), maintaining the total percentage of osmolites equal to 1.5%. The results are summarized in Table 4.

Table 5, on the other hand, gives the composition of the amino acids used. The composition of the amino acid solution is the optimal composition to minimize the metabolic acidosis that may occur when such solutions are used.

TABLE 4

Percentage changes in fluid volume recovered from rats submitted to peritoneal dialysis with 15 ml of solution containing different mixtures of carnitine, glucose and amino acids (aa).

| Solutions | % increase in volume (2 h) | % increase in volume (4 h) | % increase in volume (6 h) |
|---|---|---|---|
| Carnitine 1.5% | 25.8 ± 1.3 | 22.5 ± 1.6 | 25.3 ± 1.4 |
| Glucose 1.5% | 21.1 ± 1.5 | 21.5 ± 1.9 | 21.7 ± 1.6 |
| Car + Glu 1.0 + 0.5% | 25.6 ± 1.6 | 28.4 ± 1.6 | 27.6 ± 1.5 |
| Car + aa 0.5 + 1.0% | 24.6 ± 1.2 | 26.4 ± 1.3 | 25.3 ± 1.2 |
| Car + aa 0.8 + 0.7% | 23.1 ± 1.5 | 24.5 ± 1.4 | 26.0 ± 1.5 |
| Car + aa 1.0 + 0.5% | 25.9 ± 1.5 | 28.4 ± 1.5 | 33.8 ± 1.4 |

Results are expressed as mean (n=3)±S.D.

The fluid recovery in the first 2 h is comparable for all solutions assayed and ranges from 21.7 to 25.9%. Moreover, this increase remains constant at the later observation times (4 and 6 h) for all solutions, except for a tendency to increase over time in the case of the solution containing Car+aa (1.0+0.5%).

TABLE 5

Composition of solution containing aa

| Amino acids | Concentration (mg %) |
|---|---|
| Leucine | 74–112 |
| Valine | 100–151 |
| Threonine | 47–71 |
| Isoleucine | 61–92 |
| Lysine HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 |
| Phenylalanine/Tyrosine | 1.3–3.0 |
| Generating/neutralizing acids | 1–2.2 |
| Essential/Total | 0.4–0.7 |

The following examples further illustrate the invention.

EXAMPLE 1

Solution for peritoneal dialysis

| Sodium | 134.0 mmol/l |
|---|---|
| Calcium | 1.75 mmol/l |
| Magnesium | 0.5 mmol/l |
| Chloride | 103.5 mmol/l |
| Bicarbonate | 34.0 mmol/l |
| L-carnitine | 1.5% |

EXAMPLE 2

Solution for peritoneal dialysis

| Sodium | 134.0 mmol/l |
|---|---|
| Calcium | 1.75 mmol/l |
| Magnesium | 0.5 mmol/l |
| Chloride | 103.5 mmol/l |
| Bicarbonate | 34.0 mmol/l |
| L-carnitine | 2.5% |

EXAMPLE 3

Solution for peritoneal dialysis

| Sodium | 134.0 mmol/l |
|---|---|
| Calcium | 1.75 mmol/l |
| Magnesium | 0.5 mmol/l |
| Chloride | 103.5 mmol/l |
| Bicarbonate | 34.0 mmol/l |
| L-carnitine | 4.25% |

EXAMPLE 4

Solution for peritoneal dialysis

| Sodium | 134.0 mmol/l |
|---|---|
| Calcium | 1.75 mmol/l |
| Magnesium | 0.5 mmol/l |
| Chloride | 103.5 mmol/l |
| Lactate | 35.0 mmol/l |
| L-carnitine | 1.0% |
| Glucose | 0.5% |

EXAMPLE 5

Solution for peritoneal dialysis

| Sodium | 134.0 mmol/l |
|---|---|
| Calcium | 1.75 mmol/l |
| Magnesium | 0.5 mmol/l |
| Chloride | 103.5 mmol/l |
| Bicarbonate | 34.0 mmol/l |
| L-carnitine | 1.0% |

Mixture of Amino acids as in Table 5 0.5%

EXAMPLE 6

Solution for twin-bag peritoneal analysis

Bag 1

| Sodium | 193.0 mmol/l |
|---|---|
| Calcium | 1.75 mmol/l |
| Magnesium | 0.5 mmol/l |
| Chloride | 103.5 mmol/l |
| Lactate | 35.0 mmol/l |
| Glucose | 0.5–4.0% |

Bag 2

-continued

| | | |
|---|---:|---|
| Bicarbonate | 34.0 | mmol/l |
| L-carnitine | 4.0–0.5% | |

EXAMPLE 7

Solution for peritoneal dialysis

| | | |
|---|---:|---|
| Sodium | 134.0 | mmol/l |
| Potassium | 2.0 | mmol/l |
| Calcium | 1.75 | mmol/l |
| Magnesium | 0.5 | mmol/l |
| Chloride | 105.5 | mmol/l |
| Bicarbonate | 34.0 | mmol/l |
| L-carnitine | 1.5–4.25% | |

EXAMPLE 8

Solution for peritoneal dialysis

| | | |
|---|---:|---|
| Sodium | 134.0 | mmol/l |
| Potassium | 2.0 | mmol/l |
| Calcium | 1.75 | mmol/l |
| Magnesium | 0.5 | mmol/l |
| Chloride | 105.5 | mmol/l |
| Lactate | 35.0 | mmol/l |
| L-carnitine | 0.5–4.0% | |
| Glucose | 4.0–0.5% | |

What is claimed is:

1. A method of using L-carnitine and/or its alkanoyl derivatives in peritoneal dialysis comprising administering to a subject a solution comprising about 0.5% w/v to about 10% w/v of L-carnitine and/or its alkanoyl derivatives, in which the alkanoyl is a straight or branched aliphatic group, with 2 to 8 carbon atoms, optionally in the form of a pharmaceutically acceptable salt, as an osmotic agent.

2. The method according to claim 1, in which said osmotic agent is L-carnitine.

3. The method according to claim 1, in which said osmotic agent is acetyl L-carnitine.

4. The method according to claim 1, where said osmotic agent is a combination of L-carnitine and at least one of its alkanoyl derivatives.

5. The method according to claim 4, in which said alkanoyl derivative is acetyl L-carnitine.

6. The method according to claim 1, in which at least one additional osmotic agent is present in the solution.

7. The method according to claim 1, in which glucose is also present in the solution.

8. The method of claim 2, in which the solution contains about 0.7 to about 7% w/v L-carnitine.

9. The method of claim 2, in which the solution contains about 1 to about 5% w/v L-carnitine.

10. The method of claim 2, in which the solution contains about 0.5% w/v L-carnitine.

11. The method of claim 2, in which the solution contains about 2.5% w/v L-carnitine.

12. The method of claim 2, in which the solution contains about 4.25% w/v L-carnitine.

13. The method of claim 7, in which the solution contains about 0.5% glucose and about 1.0% w/v L-carnitine.

\* \* \* \* \*